United States Patent [19]
Haber et al.

[11] Patent Number: 5,378,233
[45] Date of Patent: Jan. 3, 1995

[54] SELECTED DOSE PHARMACEUTICAL DISPENSER

[75] Inventors: Terry M. Haber, Lake Forest; Clark B. Foster, Laguna Hills; William H. Smedley, Lake Elsinore, all of Calif.

[73] Assignee: Habley Medical Technology Corporation, Laguna Hills, Calif.

[21] Appl. No.: 977,754

[22] Filed: Nov. 18, 1992

[51] Int. Cl.⁶ .................. A61M 37/00; A61M 5/20; A61M 5/315

[52] U.S. Cl. .................. 604/83; 604/90; 604/135; 604/191; 604/211; 604/237

[58] Field of Search ............ 604/56, 68, 71, 72, 604/82, 89, 90, 83, 134, 135, 152, 183, 187, 189, 191, 192, 207, 208, 211, 220, 224, 228, 232, 236, 237, 239, 246, 247, 249

[56] References Cited

U.S. PATENT DOCUMENTS

| | | |
|---|---|---|
| ,273,257 | 6/1981 | Smith et al. . |
| 3,162,217 | 12/1964 | Poli, Jr. et al. . |
| 3,248,950 | 5/1966 | Pursell et al. . |
| 3,283,727 | 11/1986 | Rodrigues, Jr. . |
| 3,343,539 | 9/1967 | Moorhouse . |
| 3,831,602 | 8/1974 | Broadwin . |
| 4,040,420 | 8/1977 | Speer . |
| 4,044,757 | 8/1977 | Whorter et al. ............ 604/191 |
| 4,190,048 | 2/1980 | Sampson ............ 604/236 X |
| 4,381,778 | 5/1983 | Kozam et al. . |
| 4,610,666 | 9/1986 | Pizzino ............ 604/191 |
| 4,623,332 | 11/1986 | Lindmayer et al. ............ 604/68 |
| 4,631,055 | 12/1986 | Redl et al. . |
| 4,666,430 | 5/1987 | Brown et al. . |
| 4,689,042 | 8/1987 | Sarnoff et al. ............ 604/89 |
| 4,795,433 | 1/1989 | Sarnoff ............ 604/134 |
| 4,801,434 | 1/1989 | Kido et al. . |
| 4,846,405 | 7/1989 | Zimmerman . |
| 4,874,368 | 10/1989 | Miller et al. . |
| 4,883,472 | 11/1989 | Michel . |
| 4,931,044 | 6/1990 | Beiter ............ 604/248 |
| 4,962,868 | 10/1990 | Borchard . |
| 4,978,336 | 12/1990 | Capozzi et al. . |
| 5,019,048 | 5/1991 | Margolin . |
| 5,042,977 | 8/1991 | Bechtold et al. ............ 604/134 |
| 5,078,691 | 1/1992 | Hamacher ............ 604/191 |
| 5,112,317 | 5/1992 | Michel ............ 604/208 |
| 5,114,406 | 5/1992 | Gabriel et al. ............ 604/136 |
| 5,226,895 | 7/1993 | Harris ............ 604/208 |
| 5,226,896 | 7/1993 | Harris ............ 604/211 |

FOREIGN PATENT DOCUMENTS

| | | |
|---|---|---|
| 313519 | 4/1989 | European Pat. Off. . |
| 984352 | 5/1951 | France . |
| 1054173 | 9/1954 | France . |
| 1051010 | 12/1954 | France . |
| 137660 | 10/1901 | Germany . |
| 245816 | 5/1987 | Germany . |
| 733168 | 6/1955 | United Kingdom . |

OTHER PUBLICATIONS

Brochure "How to Use Your *NovolinPen* TM," Sep. 1990, Novo Nordisk A/S.

Brochure "Product Information for the *NovoPen*®  Insulin Delivery System," issue 1988, Squibb–Novo, Inc.

Brochure "Product Information for the *NovolinPen* TM Insulin Delivery System," issued 1988, Squibb–Novo, Inc.

*Primary Examiner*—John D. Yasko
*Assistant Examiner*—Adam J. Cermak
*Attorney, Agent, or Firm*—Townsend & Townsend Khourie & Crew

[57] ABSTRACT

A dispenser (2) includes a body (4), a needle (110) and one or more hollow cylinders (28) and pistons (144). The needle is movable between predelivery position and a delivery position, at which the inner needle end (112) opens a ball check valve (142) to permit free fluid flow from the cylinder, along a flow path (46) and through the needle. A threaded dose adjuster (164, 166) is mounted within the body and engages a threaded stem (150). The stem is prevented from rotating so that a rotation of the dose adjuster in one direction causes the dose adjuster to move axially away from the piston to compress a drive spring (176) and preload the stem. Moving the needle assembly to the delivery position causes the dose of pressurized pharmaceutical to be automatically driven from the cylinder and through the needle. The cylinder can be refilled by the user through the needle by opening (88, 92, 94) a supplemental pathway (54, 52) and rotating the dose adjuster in the opposite direction.

37 Claims, 10 Drawing Sheets fig. 1A fig. 1B fig. 2 fig. 2A fig. 2B fig. 3 fig. 3A fig. 3D fig. 3E

SELECTED DOSE PHARMACEUTICAL DISPENSER

CROSS REFERENCE TO RELATED APPLICATIONS

This is related to the following U.S. patent applications: Ser No. 07/931,777, filed Aug. 18, 1992, for Reusable Pharmaceutical Dispenser With Full Stroke Indicator; Ser. No. 07/924,620, filed Aug. 4, 1992, titled Pharmaceutical Dispenser Assembly With a Cartridge Transfer Unit; Ser. No. 07/862,090, filed Apr. 2, 1992, titled Variable Proportion Dispenser; Ser. No. 07/808,717, filed Dec. 17, 1991, now U.S. Pat No. 5,240,146 titled Variable Proportion Dispenser; the disclosures of each of these applications is incorporated by reference.

BACKGROUND OF THE INVENTION

Frequently a physician will prescribe two or more medications to be taken by a patient either simultaneously or as close to simultaneously as practical. This is often the case in prescribing insulin. Two basic types of insulin are most frequently prescribed: regular, a fast-acting variety, and NPH, an intermediate-acting variety. Additionally, a longer-acting type of insulin called ultralente is also available. These types of insulin differ in their onset and duration of action. Regular insulin typically has the quickest onset and the briefest duration of action. The onset and duration of insulin may be modified by chemical manipulations which include precipitation with protamine or suspension with isophane or zinc. Injectable insulin is derived from pigs and cattle, and a semi-synthetic genetically-engineered human form is available commercially.

Regardless of the final chemical composition or origin of the insulin prescribed, the physician frequently advises the patient: to mix two or more types of insulin and to inject them at least once a day. Some patients respond best to a schedule of two or three daily doses, usually in conjunction with meals. Frequently trial-and-error type of evaluation is practiced to arrive at the correct dosing and combination for the individual patient. However, after this initial adjustment period, the patient may be maintained on the same dose and proportion of insulins for many weeks or months assuming that the patient's diet, activity, and state of health remain reasonably constant or predictable. An example of a typical mixture and ratio of insulins is 70% NPH and 30% regular insulin injected just prior to a meal.

The implications of insulin therapy for the patient generally include the need for two separate sets of insulin injection syringes and needles. This is because the patient will usually draw a predetermined amount of insulin from each of two vials. A sophisticated patient may be able to use a single syringe and simply draw up the correct amount from each separate insulin vial. However, he may prefer to use two separate needles because of the danger of mixing two types of insulin by using a needle "contaminated" with one type of insulin and accidentally getting some of the first insulin into the second vial from which he draws the second insulin. If the patient is riot sophisticated or not adept at drawing up insulin from a vial into a syringe, he would need two needles and two syringes. He may find that he has drawn up too much insulin and then he wishes to return the excess to the vial. If he is using a single syringe, he cannot return the excess to the vial if he is presently attempting to draw insulin from the second vial. The problem of getting the correct amount and proportion of each type of insulin prescribed is an everyday difficulty which the diabetic patient may face two or three times a day.

Besides insulin, other medications may be advantageously prescribed as a simultaneous or near-simultaneous dose. For example, pain medications of the opiate family are frequently prescribed together with antiemetics. The antiemetic drugs are often useful as potentiators of narcotic painkillers and additionally they may ameliorate some of the side effects of narcotics such as nausea and vomiting. For example, a patient who has chronic pain, such as that associated with metastatic cancer, may take 50 milligrams of meperidine (a narcotic) and 25 milligrams of hydroxyzine (an antiemetic) intramuscularly several times a day. Patients having chronic pain are often managed in a long-term care facility such as a nursing home. Alternatively, an outpatient setting is sometimes feasible if the patient or his family can administer medications.

Unfortunately, many patients requiring either chronic pain medication or insulin find that they have some difficulty with their eyesight. This may be especially true of the older age group. Additionally, diabetics who require insulin replacement frequently suffer deterioration of vision as a consequence of the diabetic process. Thus, people who are often in greatest need of multiple injected medications of a defined dose and proportion may ironically find their drug regimen most difficult to regulate precisely. Another problem arises in the context of long-term care facilities such as nursing homes. Frequently the nurse who administers injectable drugs is pressed for time on medication rounds. The time pressure is compounded if the care facility is constrained by budgetary or other non-medical concerns. A device which permits accurate dosing and proportion of two or more medications could be useful to a variety of patients in a variety of circumstances.

SUMMARY OF THE INVENTION

This invention is directed to a liquid pharmaceutical dispenser from which the user can select the dose easily and accurately. It is particularly adaptable for use in delivering two or more liquid pharmaceuticals during a single injection. It also allows the user to automatically inject a preselected dose while shielding the needle prior to use. The dispenser can be provided to the user empty; this permits the user to fill the dispenser with his or her specific liquid pharmaceuticals.

The dispenser includes a body to which a needle assembly, or other pharmaceutical dispensing head, is mounted. One or more hollow cylinders (typically round), and a piston mounted within each cylinder, are mounted within the body. The piston and the hollow cylinder define a pharmaceutical chamber containing a liquid pharmaceutical. A fluid flow path couples the pharmaceutical chamber and the needle assembly. A first check valve, used when two or more pharmaceutical cartridges are used, is at one end of the flow path adjacent the pharmaceutical chamber. The first check valve permits fluid flow from the, pharmaceutical chamber into the flow path, but not the reverse. A second valve, preferably in the form of a ball check valve, is used along the flow path to normally prevent fluid flow along the flow path from the pharmaceutical chamber, along the flow path and to the needle assembly. In a preferred embodiment, the needle assembly is movable between a predelivery position, at which the ball check valve halts fluid flow along the flow path from the pharmaceutical chamber to the needle assembly, and a delivery position, at which the double ended needle cannula of the needle assembly biases the ball of the ball check valve away from the valve seat, thus permitting free fluid flow from the pharmaceutical chamber, along the flow path and through the needle cannula.

The distal end of a threaded stem is mounted to the piston. A hollow dose adjuster is mounted within the body. The dose adjuster includes internal threads which engage the external threads on the stem. The stem is prevented from rotating so that a rotation of the dose adjuster causes relative axial movement of the stem and dose adjuster. When the needle assembly is in the predelivery position, so that the ball check valve is closed, the stem is prevented from driving the piston through the cylinder. Accordingly, rotational movement of the dose adjuster causes the dose adjuster to move axially while the stem remains stationary. Rotating the dose adjuster (typically clockwise) so that the dose adjuster moves away from the piston causes a drive spring, which engages a flange on the dose adjuster, to compress. This compression preloads the stem so that moving the needle assembly from the predelivery position to the delivery position causes the dose of pharmaceutical to be automatically driven from the pharmaceutical chamber, past the first check valve, along the flow path, past the ball check valve and through the double-ended needle cannula.

The movement of the dose adjuster corresponds to the dose of the pharmaceutical. In the preferred embodiment, the axial movement is monitored using a rack and pinion arrangement. The dose adjuster has a series of annular grooves along its surface, which are engaged by the teeth of a display pinion. The annular grooves act like a circular rack so that axial movement of the dose adjuster causes rotary movement of the display pinion. The display pinion rotates a display disk having a numerical values around its outer edge. The numerical values are visible through a window in the body to indicate the units of liquid pharmaceutical to be dispensed.

The flange on the dose adjuster engages stop ledges formed within the body to limit the proximal and distal movement of the dose adjuster.

The pharmaceutical chamber can be refilled by the user by the manipulation of an aspiration valve control plate. Doing so opens a supplemental pathway coupling the flow path and the pharmaceutical chamber, thus bypassing the first check valve. The user then places the needle assembly in the delivery position, rotates the dose adjuster in, for example, the counterclockwise direction, thus pulling the piston proximally to pull the replacement liquid pharmaceutical into the pharmaceutical chamber.

Safety is enhanced using a needle shield slidably mounted to the body. The needle shield is normally maintained in a safe position at which the needle assembly is shielded by being housed within the needle shield . Just prior to use, the needle shield is manually released from its safe position and moved to its use position, thus exposing the outer end of the needle cannula. Preferably, this occurs as a single operation in which the needle shield is released from its safe position, preferably by pressing two release buttons simultaneously, and is driven towards its use position by pushing the distal end of the needle shield against the patient. This drives the distal end of the double ended needle cannula into the patient. At the end of the movement of the needle shield, the proximal end of the double ended needle cannula dislodges the ball from the seat of the ball check valve allowing the automatic pressurized injection of the selected pharmaceutical dose under the influence of the drive spring.

One of the primary advantages of the invention is that it is relatively simple in construction, reusable and can be filled by the user for enhanced economy.

Other features and advantages of the invention will appear from the following description in which the preferred embodiment has been set forth in detail in conjunction with the accompanying drawings.

DESCRIPTION OF THE PREFERRED EMBODIMENT

Figure 1A:
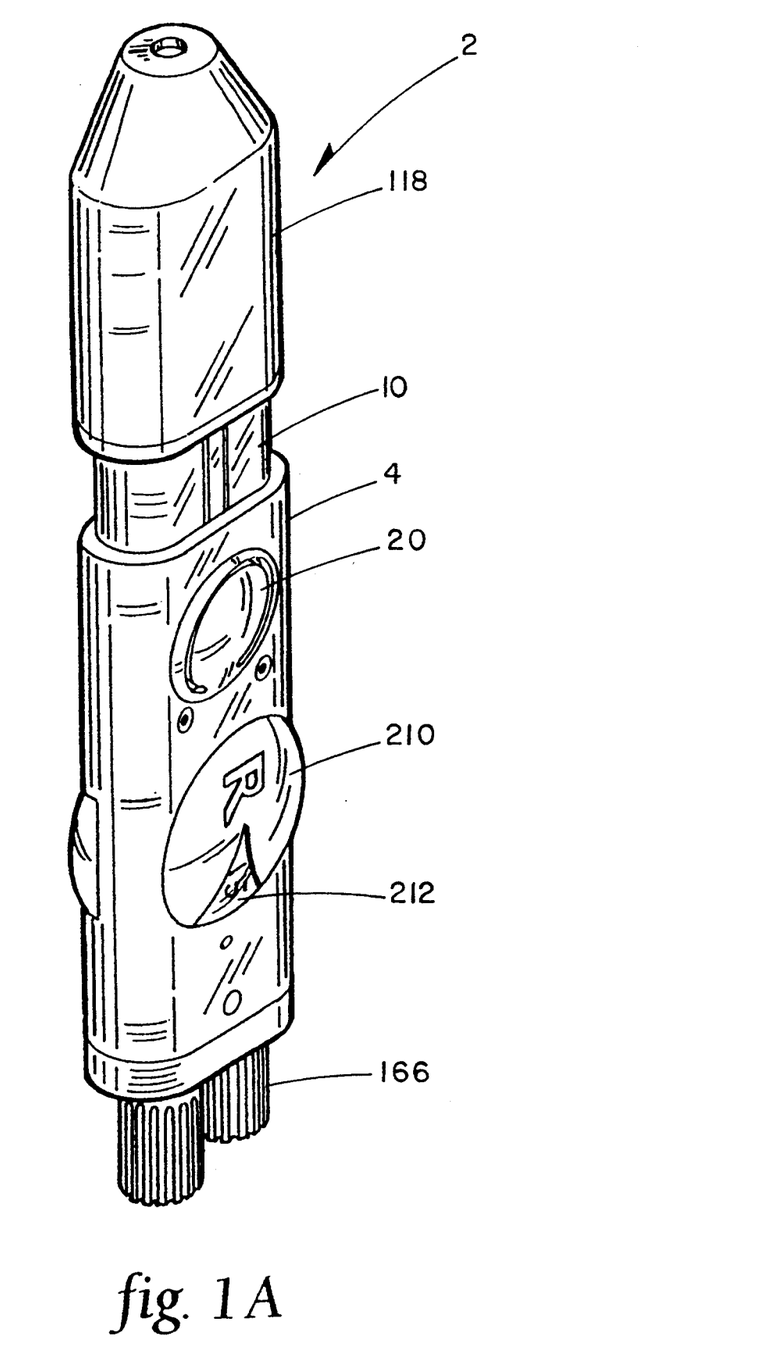
FIGS. 1A and 1B are overall assembled views of a selected dose dual pharmaceutical dispenser made according to the invention with the shield in the safe and use positions respectively.
Figure 1B:
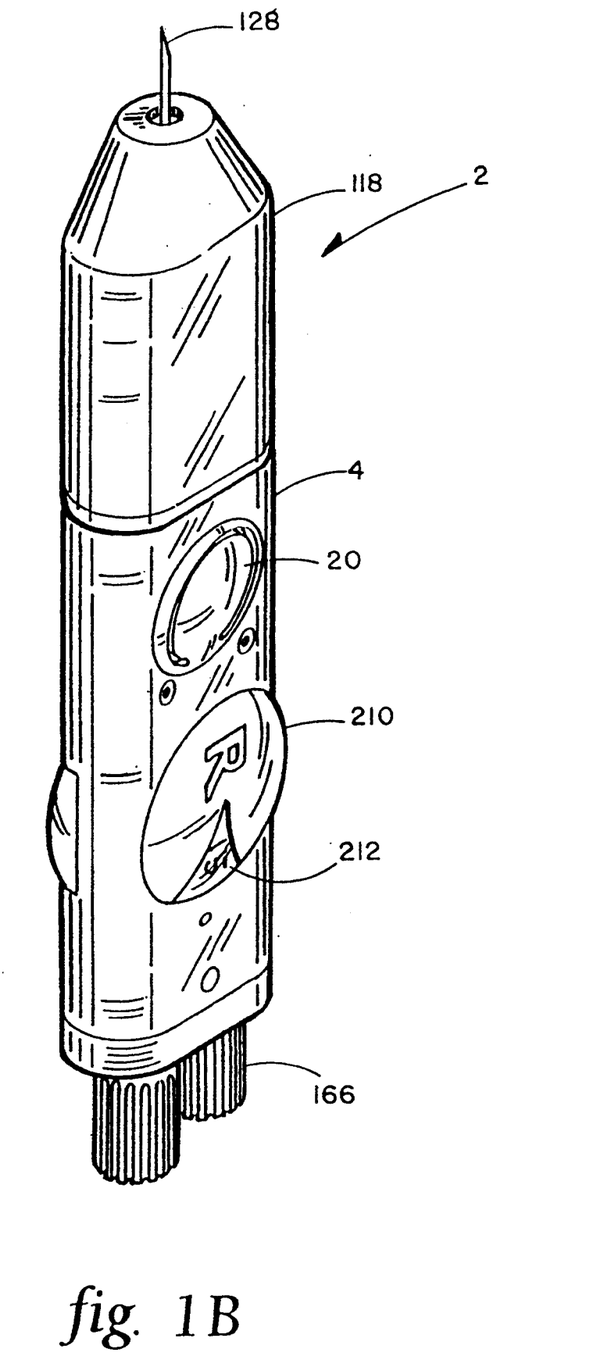
Figure 2:
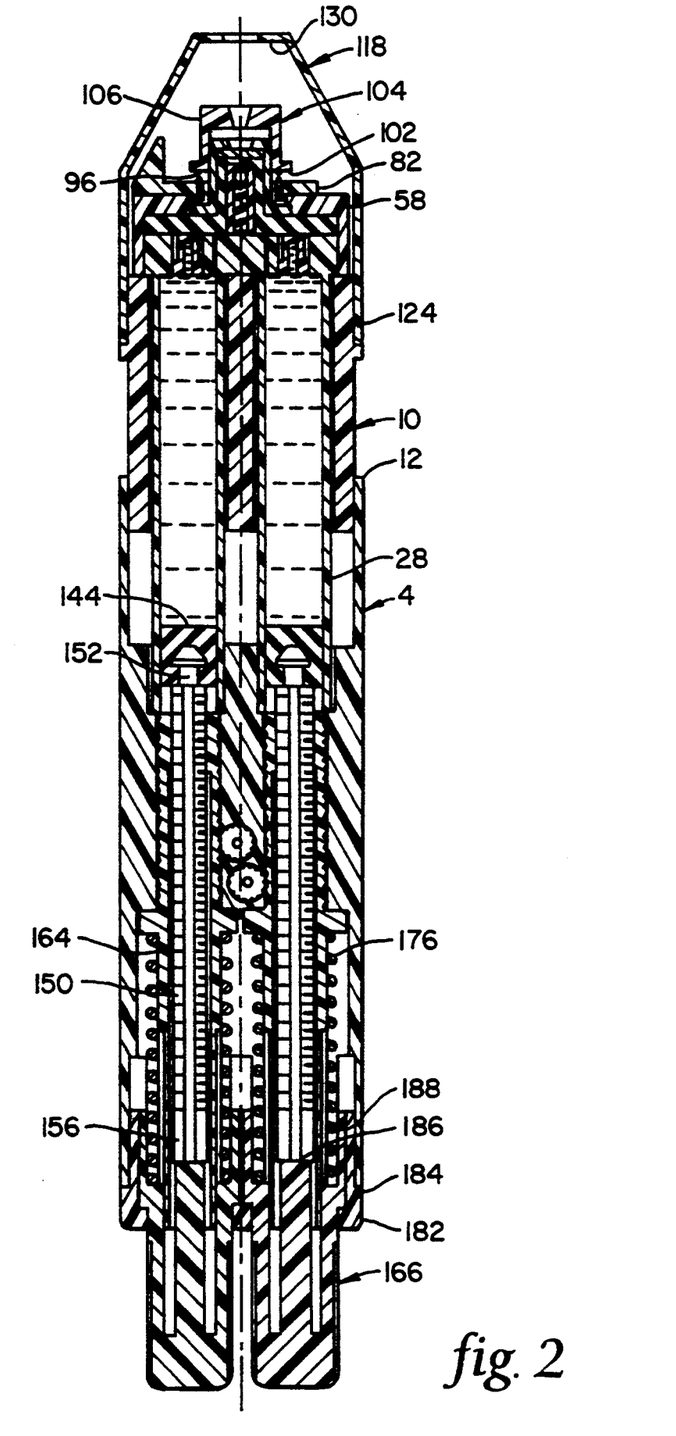
FIG. 2 is a cross-sectional view of the dispenser of FIG. 1 shown without the double-ended needle cannula assembly and with the pharmaceutical chambers filled with a pharmaceutical.
Figure 2A:
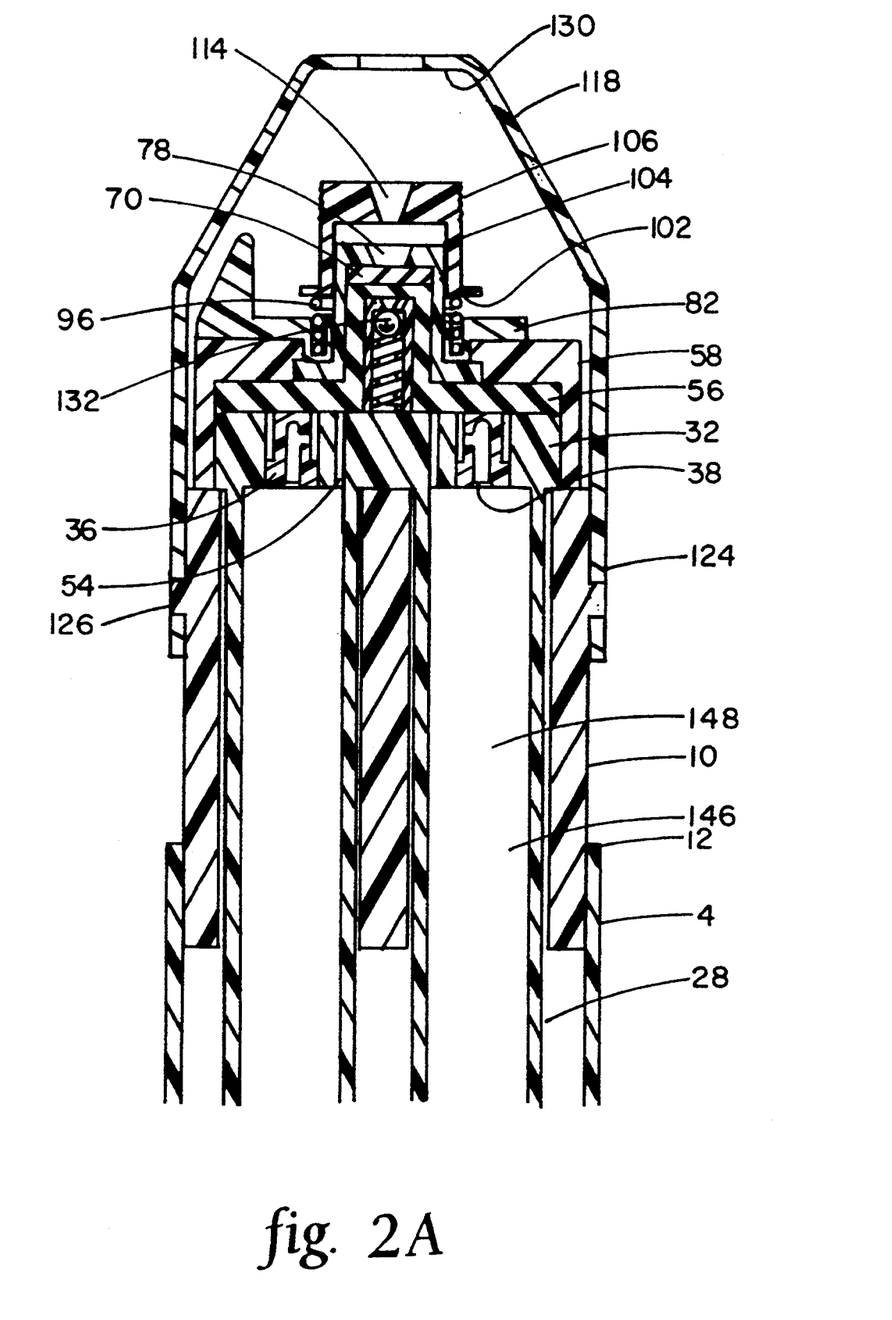
FIGS. 2A and 2B are enlarged views of the distal and proximal portions of the dispenser of FIG. 2.
Figure 2B:
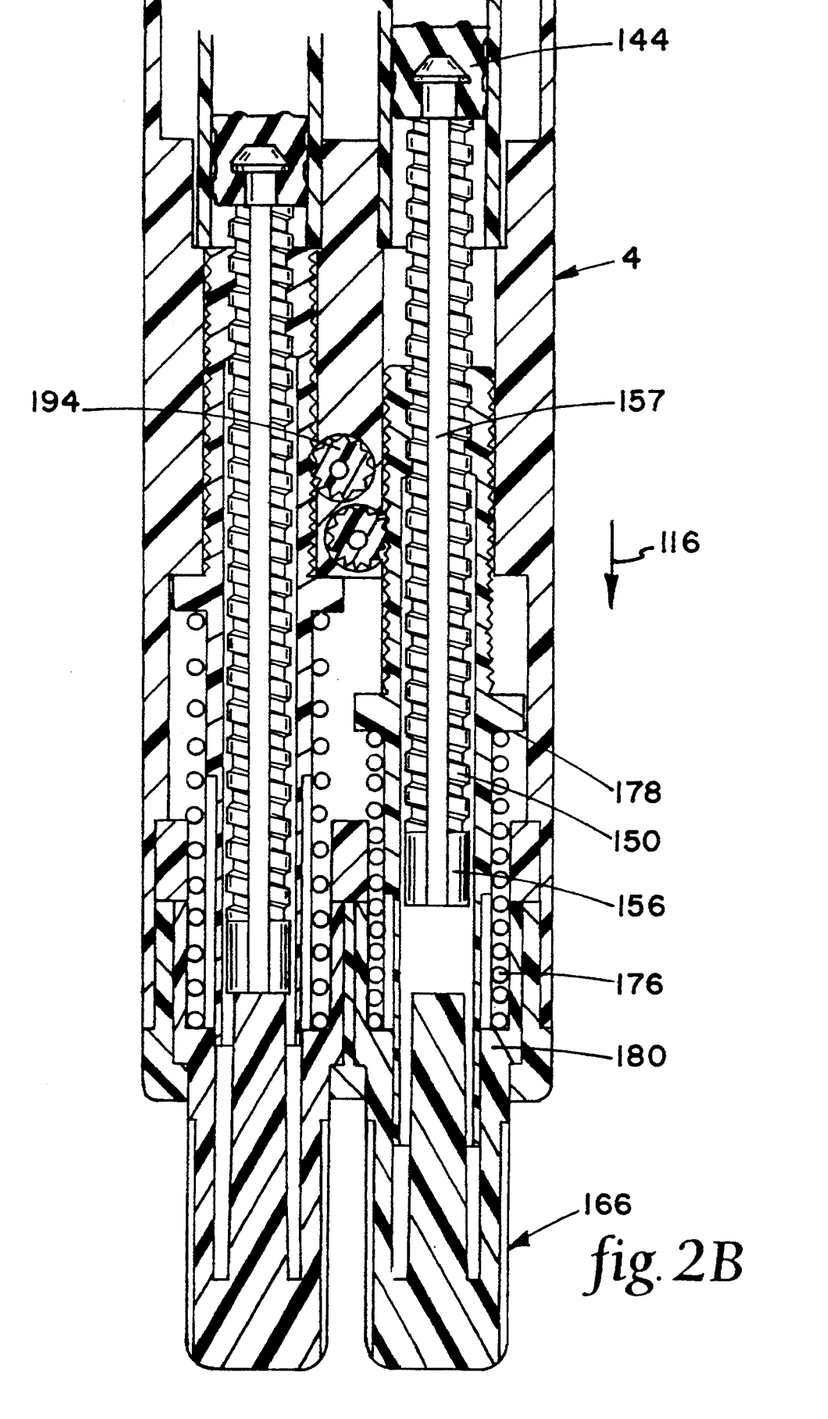
Figure 3:
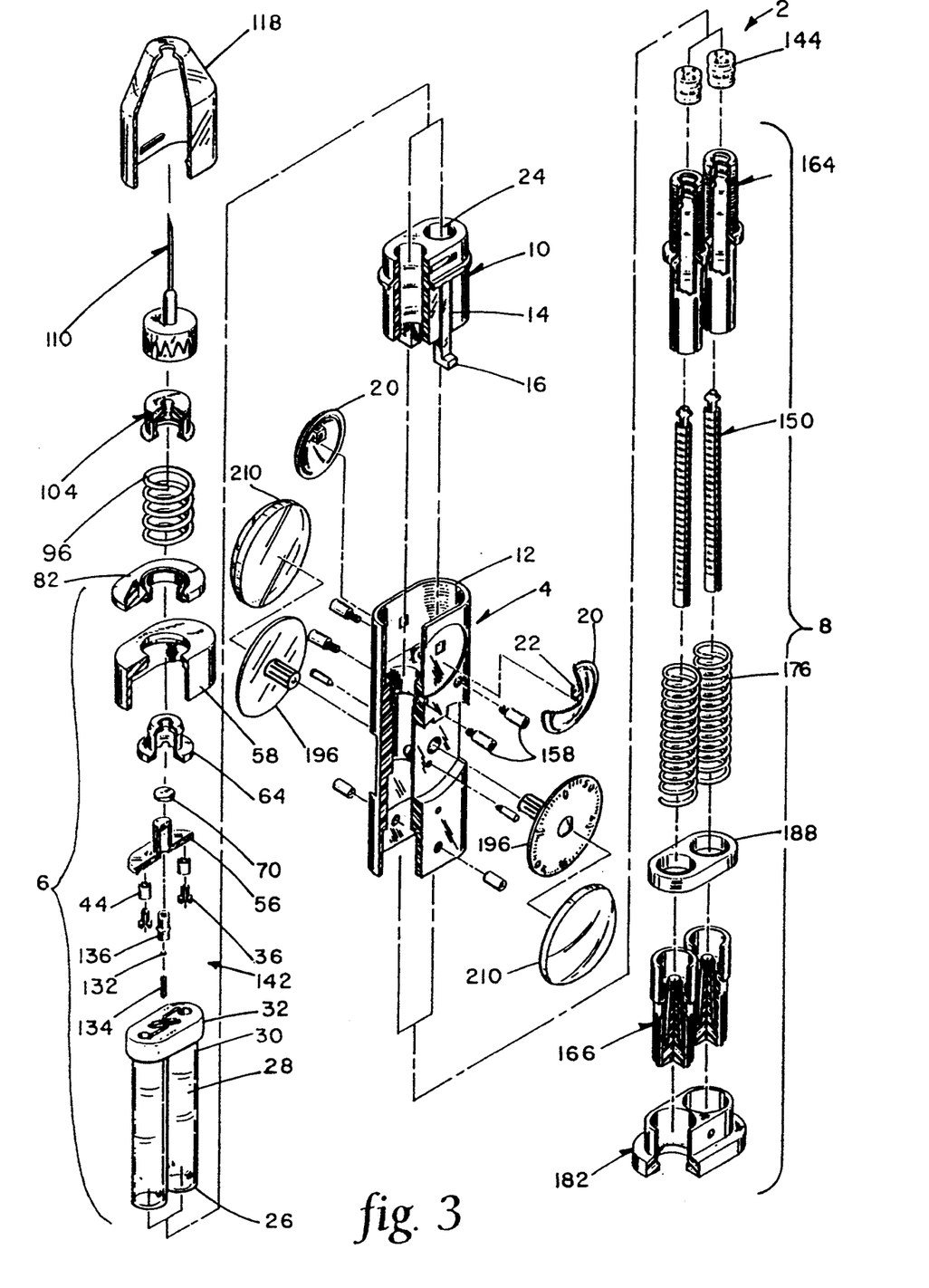
FIG. 3 is an exploded isometric view of the dispenser of FIG. 2, including a double-ended needle cannula assembly.

Referring the reader to FIGS. 1-3, a selected dose dual pharmaceutical dispenser 2 is seen to include a main body 4 housing a dual cartridge-type assembly 6 and a dosing assembly 8. A sliding body 10 is slidably mounted within the distal end 12 of main body 4. Sliding body 10 has a pair of spring arms 14 with extensions 16 at the distal ends sized to engage complementary openings 18 formed in body 4. Spring arms 14 are biased inwardly, thus forcing extensions 16 from openings 18, when it is desired to move sliding body 10 within main body 4 for purposes to be discussed below. This is accomplished using a flexible release cover 20 on either side or body 4. Release cover 20 has an extension 22 sized and positioned to pass through opening 18 when release cover 20 is biased inwardly by the user thus pushing extension 16 from openings 18.

Sliding body 10 also includes a pair of bores 24 sized to accept the proximal ends 26 of cartridge-type cylinders 28. Although in the preferred embodiment cylinders 28 are circular in cross section, they could be other shapes, for example oval. Cylinders 28 are joined at their distal ends 30 by a manifold block 32. Manifold block 32 is, in the preferred embodiment, formed as a single piece with cylinders 28. However, it can be made separately from cylinders 28. Manifold block 30 has bores 34 with enlarged distal ends. Bores 34 provide a fluid path into the interiors of cylinders 28. The enlarged outer ends of bores 34 are sized to accept a valve insert 36, seen best in FIG. 3C. Valve insert 36 has a blind bore 38 formed therein with a radial access port 40 coupling a reduced diameter end 42 of insert 36 with blind bore 38. A cylindrical elastic band 44, made of a suitable pharmaceutical-compatible elastomeric material, is mounted over reduced diameter end 42 thus creating a check valve. That is, fluid flow can proceed from the interior of cylinders 28, through bores 34, through blind bore 38, and out access port 40. However, fluid flow in the opposite direction is prevented.

Manifold block 32 also has connecting grooves 46 formed in its upper surface 48 which connect bores 34 to a central position 50 along surface 48. An additional recess 52 is also formed in upper surface 48 connecting bypass ports 54 formed in manifold block 32. Bypass ports 54 connect recess 52 with the interiors of cartridges 28. Purpose of bypass ports 54 will be discussed below with reference to aspirating liquids into cylinders 28.

An elastomeric valve membrane 56 is mounted over surface 48 and is secured in place with a manifold case 58. Membrane 56 has an extended peripheral edge 60 which seals membrane 56 against surface 48 while permitting fluid flow along grooves 46 and recess 52. Membrane 56 also has an extended, hollow portion 62 sized to accept the proximal end of a double ended needle cannula as is discussed below.

Dual cartridge-type assembly 6 also includes an aspiration control cylinder 64 having a distal end 66 which passes through a central opening 68 in manifold case 58. Control cylinder 64 is hollow and fits over extended portion 62 of manifold membrane 56. A self-healing septum 70, made of a conventional elastomeric material which reseals itself after being punctured by the needle, is captured between a distal end 72 of membrane 56 and an inner ledge 74 at the distal end 76 of aspiration control cylinder 64. Control cylinder 64 also includes a tapered needle access port 78 through which the proximal end of a double ended needle cannula can pass.

Figure 3A:
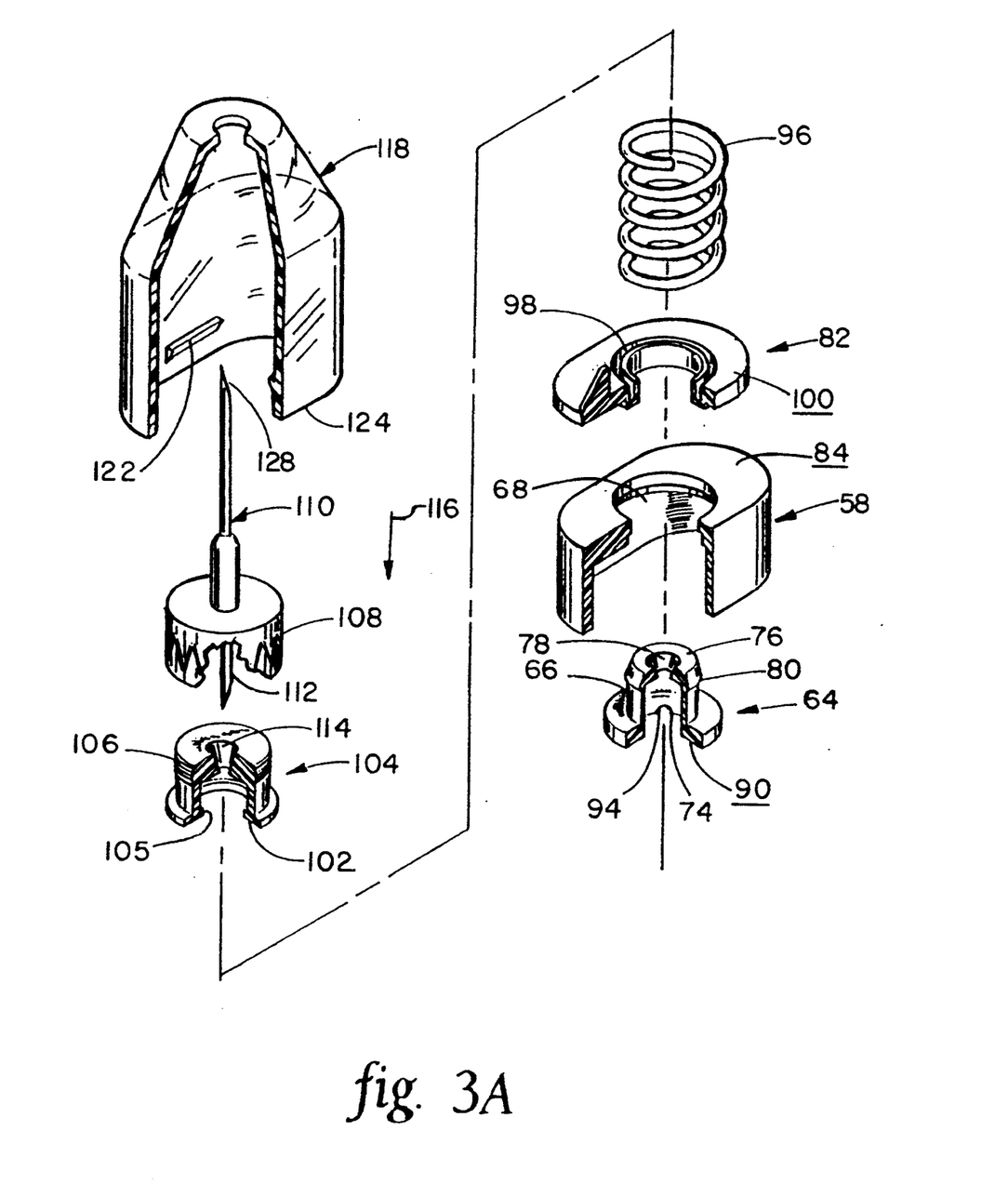
FIGS. 3A-3E are enlarged views of the various component parts shown in FIG. 3.
Figures 3B, 3C:
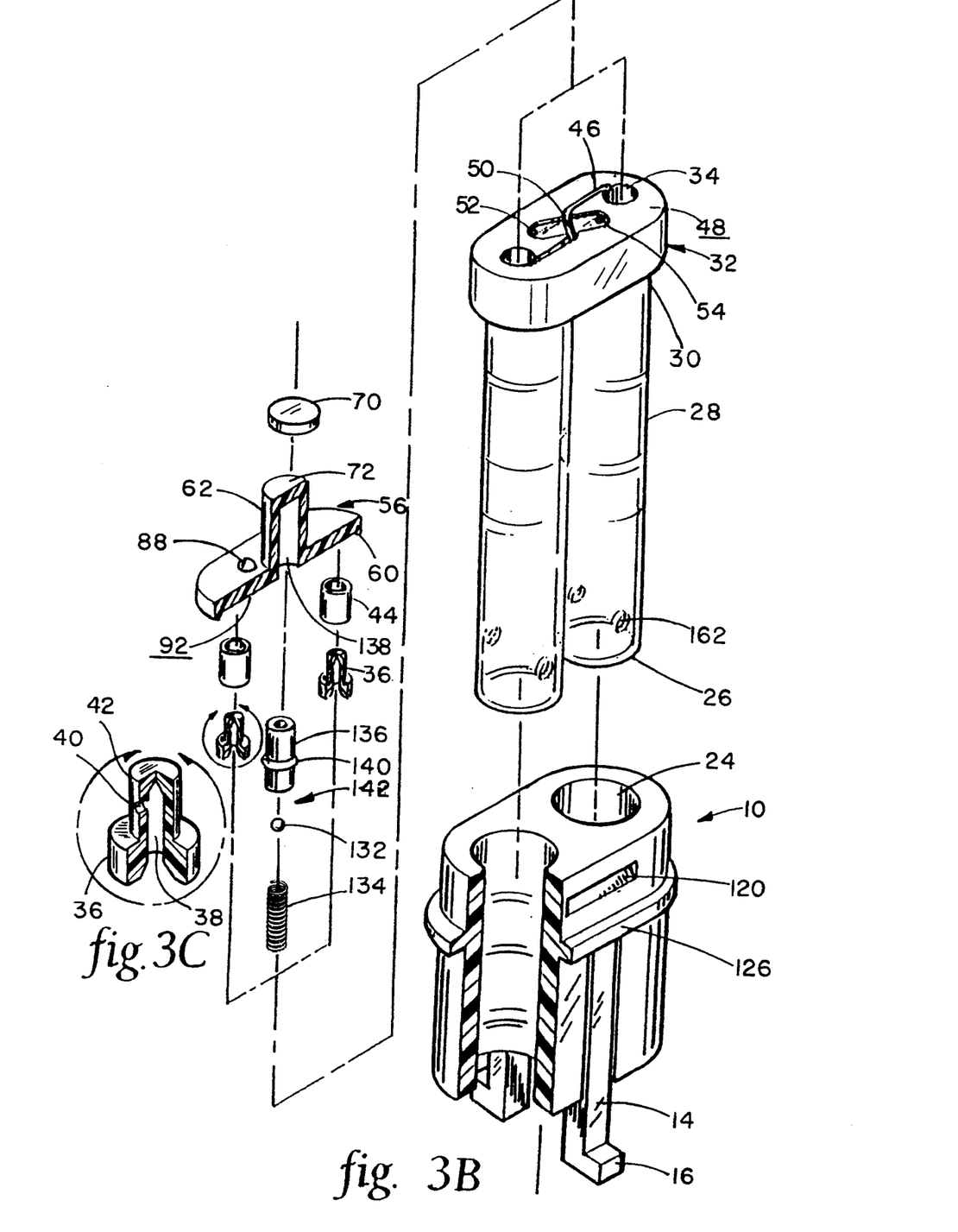
Figure 3D:
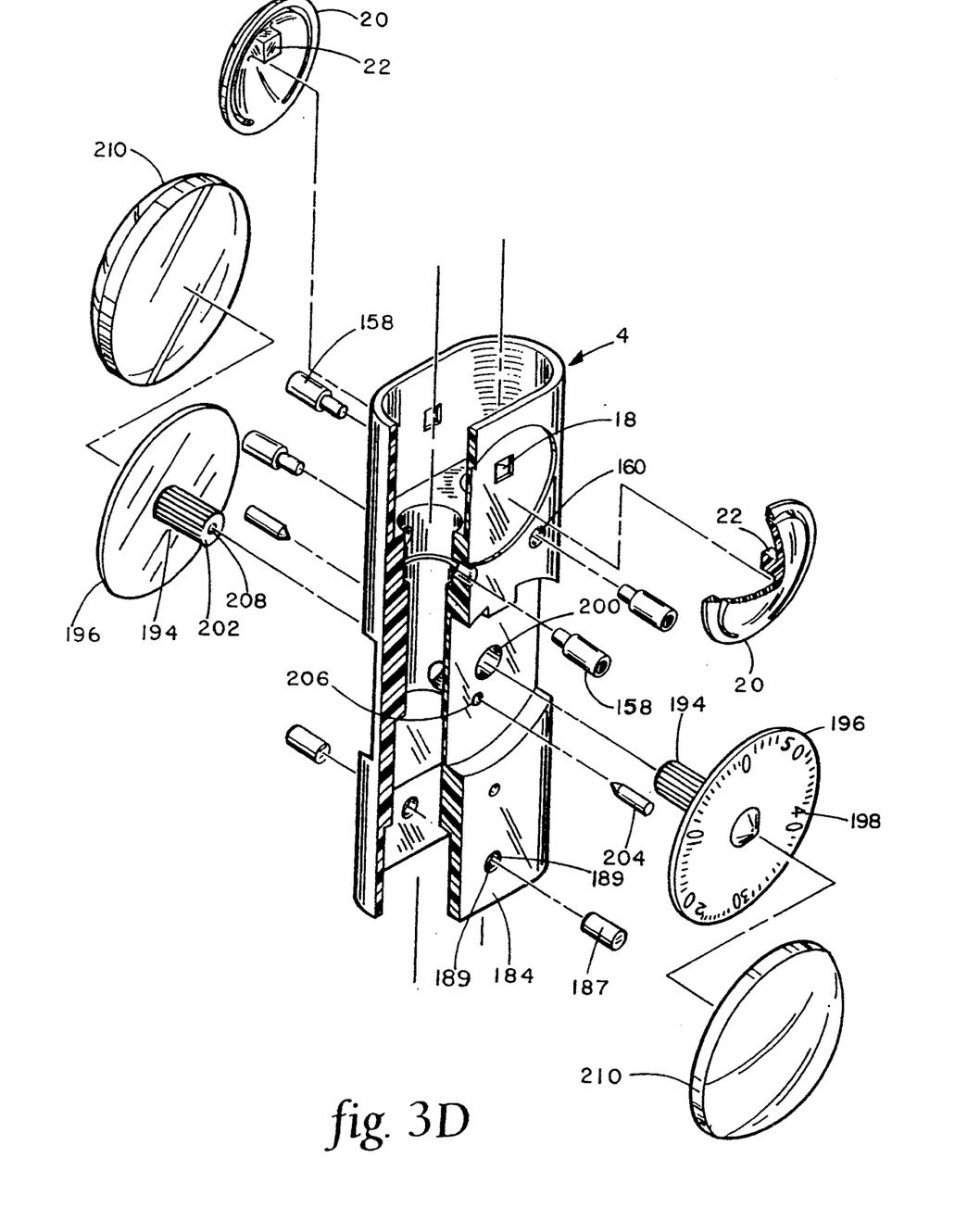
Figure 3E:
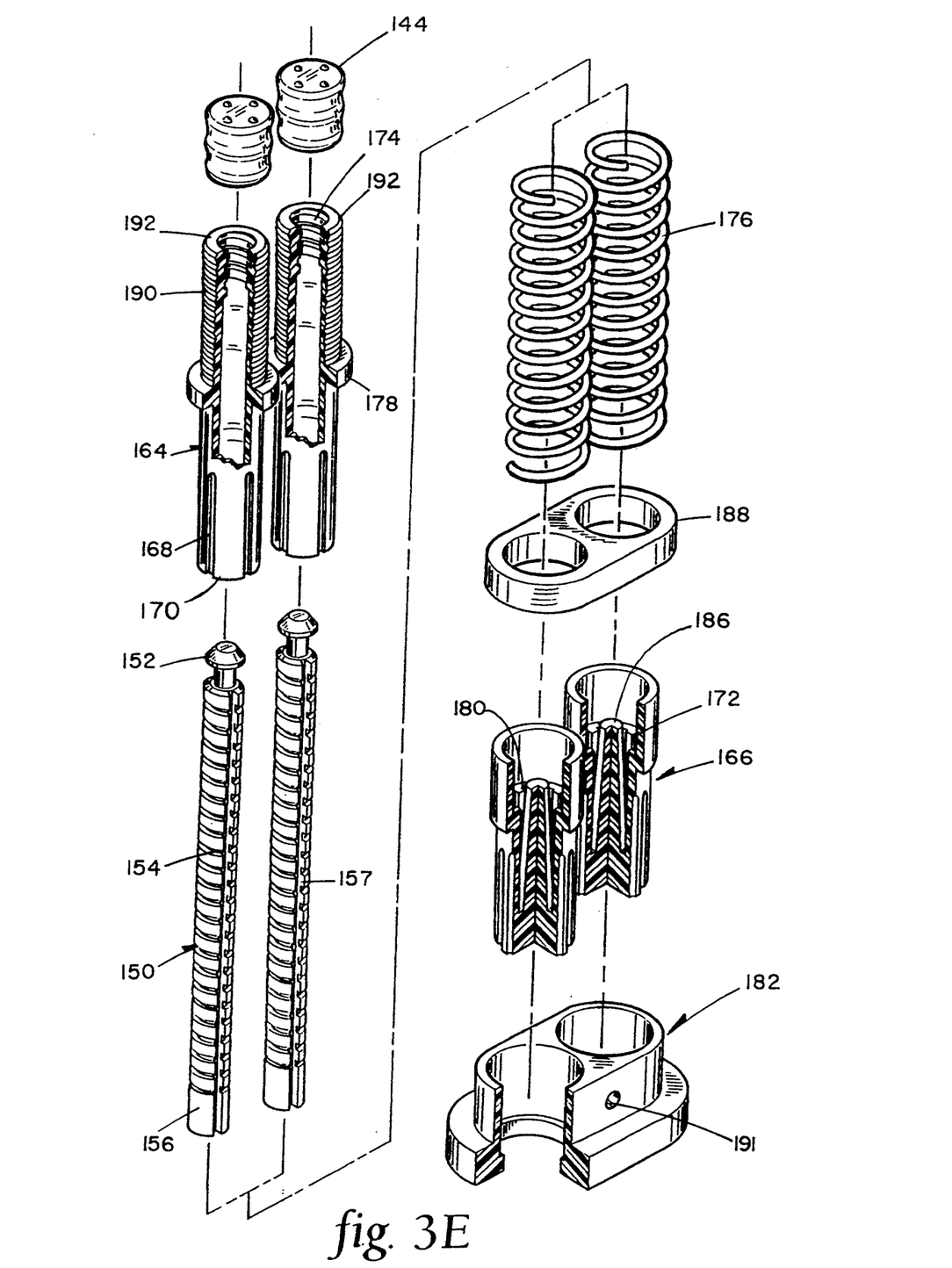

Referring to FIGS. 2A, 3A and 3B, membrane 56 includes a pair of raised bumps 88 positioned above ports 54. Normally, that is when plate 82 is aligned with manifold case 58 as shown in FIGS. 2A and 3A, the lower surface 90 of control cylinder 64 engages and presses down on bumps 88 thus deflecting the lower surface 92 of membrane 56 against bypass ports 54 thus sealing the bypass ports. However, lower surface 90 has a cutout 94 formed therein. Cutout 94 is arranged so that when plate 82 is rotated 90° from its normal position shown in FIGS. 3A and 3B, cutout 94 selectively overlies one or the other of bumps 88 to permit lower surface 92 of membrane 56 to move away from and unseal the associated bypass port 54. This is the position used to allow aspiration of a liquid pharmaceutical into the interiors of cylinders 28 as will be discussed below. To achieve rotation of control cylinder 64 with tile rotation of control plate 82, these two elements are keyed together (not shown).

A spring 96 has one end housed in a groove 98 formed in upper surface 100 of control plate 82. The other end of spring 96 is pressed against the proximal end 102 of a telescoping needle cannula receiving sleeve 104. Sleeve 104 has a hollow interior and fits over distal end 66 of control cylinder 64. Control cylinder 64 includes a lip 80 at its distal end 76 while sleeve 104 has an internal ridge 105 at proximal end 102. Control cylinder 64 and sleeve 104 are sized to permit some axial movement of sleeve 104 from the position of FIG. 2A in a proximal direction towards cylinder 28 against the bias of spring 96.

Sleeve 104 has external threads 106 which engage internal threads formed within the base 108 of a double ended needle cannula assembly 110. Needle cannula assembly 110 has a pointed proximal end 112 which extends through a central opening 114 formed in sleeve 104. Pressing on needle cannula assembly 110 in the direction of arrow 116 causes double ended cannula assembly 110 and sleeve 104 therewith to compress spring 96 causing proximal end 112 of needle cannula 110 to pass through septum 70, end 72 and into the interior 138 of extended portion 62 of membrane 56 where end 112 displaces the ball 132 of a ball check valve 142 (discussed below); this permits fluid to flow from interior of cylinder 28, through valve insert 36, past elastic band 44, along connecting groove 46, through ball check valve 142, into proximal end 112 of needle cannula 110 and out through the tip 128 of the needle cannula.

A shield 118 is mounted to sliding body 10 and normally covers needle cannula 110 in the safe position of FIGS. 1A, 2 and 2A. In this sale position sliding body 10 is at its distal-most position with extensions 16 engaging openings 18. Sliding body 10 includes a pair of recesses 120 which accept internal wedges 122 carried by shield 118. The proximal end 124 of shield 118 engage a flange 126 of sliding body 10 while wedges 122 engaging recesses 120 keep shield 118 from being removed from sliding body 10.

To expose the tip 128 of needle cannula assembly 110, the user forces shield 118 in the proximal direction 116, having first compressed release covers 20 to permit extensions 16 to be released from openings 18, by pressing the distal end of shield 118 at the injection site. Continued movement of shield 118 in proximal direction 116 causes an internal ledge 130 of shield 118 to contact base 108 of needle cannula assembly 110 thus forcing the needle cannula assembly in proximal direction 116. This movement causes proximal end 112 of the needle cannula assembly 110 to move ball 132 against the force of a spring 134. Ball 132 and spring 134 are housed within a hollow valve seat 136.

Valve seat 136 is housed within the interior 138 of extended portion 62 of membrane 56. Valve seat 136 has a radially extending ring 140 formed along its outer surface which provides a seal between valve seat 136 and membrane 56. Thus, movement of needle cannula assembly 110 in proximal direction 116 not only causes proximal end 112 of needle cannula assembly 110 to pierce septum 70 and end 72, it also opens up ball check valve 142 created by valve seat 136, ball 132 and spring 134.

Dual cartridge-type assembly 6 also includes elastomeric pistons 144 housed within cylinders 28. Pistons 144 and cylinders 28 define pharmaceutical chambers 146 which are shown in FIG. 2 containing liquid pharmaceuticals 148.

Dosing assembly 8 includes threaded stems 150 having their distal ends 152 secured to pistons 144 as shown in FIG. 2B. Threaded stems 150 have external threads 154 along most of their lengths, with the exception of a short piston at proximal ends 156. Stems 150 also have a longitudinally extending grooves 157 along substantially the entire length of the stems. Pins 158, shown in FIGS. 3 and 3D, pass through holes 160 in body 4, through holes 162 formed in cylinders 28 adjacent proximal ends 26 of the cylinders, and into grooves 157. Pins 158 serve the dual purposes of securing cylinders 28 within main body 4 and preventing threaded stems 150 from rotating.

Dosing assembly 8 also includes dosing nuts 164 and dosing knobs 166, which together constitute a telescoping dose adjuster. Dosing nuts 164 include axially extending slots 168 at their proximal ends 170 which engage complementary splines 172 formed within dose knobs 166. Thus, rotating dose knobs 166 causes dose nuts 164 to rotate as well.

Dosing nuts 164 are hollow and have internal threads 174 which mate with external threads 154 formed on threaded stems 150. Assuming the user is rotating dose knobs 166 clockwise, dosing nuts 164 rotate about drive stems 150 causing relative axial movement between the two. However, with cylinders 28 filled with liquid pharmaceuticals 148, and with sleeve 104 in the position of FIGS. 2 and 2A, the liquid pharmaceutical prevents piston 144 from moving in a distal direction causing closing nuts 164 to move in proximal direction 116. This proximal movement is resisted by drive springs 176.

Drive springs 176 are captured between flanges 178 on dosing nuts 164 and an internal ledge 180 formed within dose knobs 166. Dose knobs 166 are secured in place at proximal end 184 of main body 4 by a knob retaining block 182 at one end and a travel stop 188 at the other. Knob retaining block 182 is secured to the proximal end 184 of main body 4 by pegs 187 housed within holes 189, 191 formed in main body 4 and block 182. The axial movement of threaded stem 150 is limited in proximal direction 116 by engagement of proximal end 156 with a travel limiter 186 within the interior of dose knobs 166. Axial movement of stem 150 is limited in the distal direction by the interference of plain end 156 of stem 150 with internal threads 174 of dosing nuts 164.

Dosing nuts 164 have circular grooves 190 between flanges 178 and digital ends 192. Circular grooves 190 act as circular racks which engage display pinions 194. Display pinions 194 are connected to display disks 196 having dose display indicia 198 on their outer surfaces. Display pinions 194 pass through openings 200 in main body 4. As seen in FIG. 2B, pinions 194 are offset from one another. The outer ends 202 of display pinions 194 are supported by support pins 204. Pins 204 are housed within holes 206 in main body 4 and openings 208 formed in outer ends 202 of display pinions 194. Accordingly, as the user rotates dose knobs 166, dosing nuts 164 rotate and move in proximal direction 116. This causes display pinions 194 to ride along circular grooves 190 thus causing the display disks to rotate. Display disk 196 is covered by a lens 210. Lens 210 provides appropriate viewport 212 to permit the user to see how much liquid pharmaceutical 148 is to be dispensed according to the rotary position of display disk 196.

The relatively large diameter of display discs 196 help to provide an easy viewing, accurate indication of the dose to be delivered. Also, viewport 212 could be magnified to further aid proper dose selection. A ratchet mechanism could be used to provide an audible and tactile indication of the dose as well.

In use, and assuming cylinders 28 are empty of liquid pharmaceutical 148, the user first removes shield 118 from sliding base 10 to expose aspiration valve control plate 82. The user then rotates control plate 82 90° which causes control cylinder 64 to rotate as well. This causes cutout 94 to overlie one of the two bumps 88 thus opening the associated fluid pathway from pharmaceutical chamber 146, through bypass port 54, along recess 52 and up into the interior of valve seat 136. The user then Kresses double ended cannula assembly 110 in proximal direction 116 forcing proximal end 112 of the needle cannula through septum 70, through end 72 and finally dislodging ball 132. This opens a fluid path from the interior of valve seat 136 through to tip 128 of needle cannula assembly 110. TiP 128 is then inserted into a supply of liquid pharmaceutical 148 and the user rotates the appropriate dose knob 166, in the preferred embodiment, counterclockwise. Doing so causes threaded stem 150 to pull piston 144 in the proximal direction 116 thus aspirating liquid pharmaceutical 148 into pharmaceutical chamber 146. Control plate 82 is then rotated 180° so that cutout 94 overlies the other of the two bumps 88. The remainder of the procedure is duplicated for the pharmaceutical to be aspirated into the other cylinder 28. Plate 82 is then rotated back to its original position of FIG. 2A thereby depressing bumps 88 and sealing bypass ports 54. It should be noted that due to the size and shape of control plate 82, shield 118 cannot be replaced onto sliding body 10 until control plate 82 has been returned to the position of FIG. 2A.

To give the injection, dose knobs 166 are rotated the desired amount, such as is ten units of the liquid pharmaceutical in one cylinder 28 and 30 units of the liquid pharmaceutical in the other cylinder. Doing so compresses springs 176. The injection is given by simply pressing shield 118 against the injection site of the patient. The initial movement of shield 118 does not cause double ended needle cannula assembly 110 to move but rather allows tip 128 to enter the tissue. Once the proper depth of tissue has been pierced, additional movement of shield 118 causes similar movement of assembly 110 in proximal direction 116 causing proximal end 112 to pierce septum 70 and end 72 and to displace ball 132. When this occurs the pressurized liquid pharmaceuticals 148 in pharmaceutical chambers 146 are forced through blind holes 38 in valve inserts 36, through access ports 40, between bands 44 and ends 42 of the valve insert, along connecting grooves 46, through the interior of valve seat 136, through the double ended needle cannula 110 and into the patient's tissue. Note that a check valve created by valve insert 36 and band 44 permits movement of the liquid pharmaceutical in this direction but not the reverse so that liquid pharmaceutical from one pharmaceutical chamber 146 would not ever enter the other pharmaceutical chamber. At the end of the dispensing cycle, dosing nuts 164 and threaded ends 150 have moved axially in a distal direction along with pistons 144. This axial movement causes display pinions 194 to rotate display disks back to their zero or initial positions.

Other modification and variation can be made to the disclosed embodiment without departing from the subject of the invention as defined in the following claims. For example, instead of a needle cannula assembly 110, other types of pharmaceutical dispensing heads, including spray heads, rollers and IV spikes, could be used. Instead of ball check valve 142, other types of user manipulable valves, not necessarily check valves, could be used to initiate the delivery of the liquid pharmaceutical. In lieu of the mechanical drive spring, other types of springs or biasing members, including pneumatic springs, could be used. While the dose adjuster is preferably a two-piece telescoping element, including dosing nuts 154 and dose knobs 166, the dose adjuster could be a one-piece element as well. Pistons 144 and cylinders 28 could be replaced by other variable volume containers, such as collapsing bags or bellows arrangements.

Also, the invention can be carried out using replaceable pre-filled pharmaceutical cartridges or empty pharmaceutical cartridges instead of the integral cylinders 28 and manifold block 32. All or part of dual cartridge-type assembly 6 could be desisted to be replaced for several reasons, including contamination, use of incompatible liquid pharmaceuticals or an increase in friction between pistons 144 and cylinders 28.

What is claimed is:

1. A liquid pharmaceutical dispenser comprising:
   a body;
   a needle assembly mountable to the body;
   a hollow cylinder and an axially moveable piston within the cylinder, the piston and hollow cylinder defining a pharmaceutical chamber;
   user actuated means for fluidly coupling a liquid pharmaceutical within the pharmaceutical chamber to the needle assembly when in an open position and for fluidly sealing the liquid pharmaceutical within the pharmaceutical chamber when in a closed position;
   means for selecting a dose of the liquid pharmaceutical to be delivered through the fluidly coupling means and the needle assembly; and
   means for automatically driving the piston against the liquid pharmaceutical, thereby driving the piston a distance corresponding to the selected dose, when the user actuated means has been switched from the closed position to the open position, whereby the dose is delivered through the needle assembly.

2. The dispenser of claim 1 wherein the body is sized to accept first and second of the hollow cylinders, dose selecting means and automatically driving means.

3. The dispenser of claim 1 wherein the fluidly coupling means further comprises check valve means for permitting fluid flow from the pharmaceutical chamber while preventing fluid flow into the pharmaceutical chamber.

4. The dispenser of claim 1 wherein the fluidly coupling means includes a flow path coupling the pharmaceutical chamber to the needle assembly.

5. The dispenser of claim 4 further comprising a check valve positioned along the flow path, the check valve configured to permit fluid flow from the pharmaceutical chamber to the flow path but to prevent fluid flow from the flow path into the pharmaceutical chamber.

6. The dispenser of claim 5 wherein the check valve includes a protrusion having a port opening into the pharmaceutical chamber and an elastic band which surrounds the protrusion and covers the port.

7. The dispenser of claim 5 further comprising bypass means for allowing a liquid pharmaceutical to be aspirated into the pharmaceutical chamber while bypassing the check valve.

8. The dispenser of claim 7 wherein the bypass means includes a supplemental pathway fluidly coupling the flow path and the pharmaceutical chamber while bypassing the check valve.

9. The dispenser of claim 8 wherein the bypass means includes aspiration valve means for selectively sealing the supplemental pathway.

10. The dispenser of claim 9 wherein the selectively sealing means includes an aspiration valve means control plate movably mounted to the body near the needle assembly.

11. The dispenser of claim 4 wherein the fluidly coupling means includes a valve element positioned along the flow path.

12. The dispenser of claim 11 wherein the valve element is a check valve.

13. The dispenser of claim 12 wherein the needle assembly includes a double ended needle cannula movably mounted to the body for movement between a predelivery position and a delivery position, and the check valve includes a valve seat and a movable element biased against the valve seat.

14. The dispenser of claim 13 wherein the needle cannula is configured to engage the movable element and move the movable element away from the valve seat when the needle cannula is moved from the predelivery position to the delivery position thereby permitting free flow of fluid from the flow path to the needle cannula.

15. The dispenser of claim 14 wherein the needle cannula is spring biased towards the predelivery position.

16. The dispenser of claim 1 further comprising means for shielding said needle assembly.

17. The dispenser of claim 16 wherein the shielding means includes a shield slidably mounted to the body movable between a safe position covering the needle assembly and a use position exposing the needle assembly.

18. The dispenser of claim 17 further comprising means for temporarily securing the shield in the safe position.

19. The dispenser of claim 1 wherein the dose selecting means includes:
   a rotatable dose adjuster having first threads;
   a stem having second threads which matingly engage the first threads; and
   means for preventing the stem from rotating within the body so that rotation of the dose adjuster causes relative axial movement between the stem and the dose adjuster.

20. The dispenser of claim 19 further comprising means for providing a visual indication of the dose selected.

21. The dispenser of claim 20 wherein the visual indication means includes a rotary display disc mounted within the body and rack and pinion means for threadably coupling the display disc to the dose adjuster so that axial movement of the dose adjuster causes corresponding rotary motion of the display disc.

22. The dispenser of claim 19 wherein the automatically piston driving means includes a compression spring.

23. The dispenser of claim 22 wherein the compression spring is captured between the dose adjuster and the body.

24. The dispenser of claim 1 further comprising means for providing a visual indication of the dose selected.

25. The dispenser of claim 1 wherein the automatically piston driving means includes a compression spring.

26. The dispenser of claim 1 wherein the dose selecting means includes a dose nut and a dose knob telescopingly coupled to one another, the dose knob extending from the body for manual access by the user.

27. A liquid pharmaceutical dispenser comprising:
   a body having a body interior, a body proximal end and a body distal end;

a pharmaceutical cartridge, mounted within the body towards the body distal end, including a hollow cylinder having a cartridge interior and a piston movably mounted within the cartridge interior, the piston and hollow cylinder defining a pharmaceutical chamber;

a needle assembly mountable to the body distal end;

means for selectively fluidly coupling the needle assembly to and fluidly sealing the needle assembly from the liquid pharmaceutical in the pharmaceutical chamber when in open and closed positions respectively;

a stem having a distal end coupled to the piston and a proximal end and external stem threads;

a user-rotatable dose adjuster, rotatably mounted within the body, including internal threads engaging the external stem threads so that rotation of the dose adjuster in a first rotary direction tends to drive the threaded stem in a distal direction towards the piston and the dose adjuster in a proximal direction away from the piston, the piston being substantially immovable in the distal direction when the pharmaceutical chamber is filled with a liquid pharmaceutical so that the dose adjuster is forced in the proximal direction;

means for biasing the dose adjuster in the distal direction so that after the dose adjuster has been rotated in the first rotary direction and the dose adjuster has moved in the proximal direction against the force of the biasing means, upon placing the selectively fluidly coupling means in the open position the biasing means forces the dose adjuster and stem therewith in the distal direction thus causing the piston to move in the distal direction forcing at least a portion of the liquid pharmaceutical from the pharmaceutical and the needle assembly is fluidly sealed from the liquid pharmaceutical in the pharmaceutical chamber, through the selectively fluidly coupling means and to the needle assembly.

28. A selected dose, multiple liquid pharmaceutical dispenser comprising:

a body;

a needle assembly mountable to the body;

hollow cylinders and an axially moveable piston within each cylinder, each piston and hollow cylinder defining a variable volume pharmaceutical chamber;

a flow path coupling the pharmaceutical chambers to the needle assembly;

a check valve associated with each of the pharmaceutical chambers and positioned along the flow path, the check valves configured to permit fluid flow from the pharmaceutical chambers into the flow path but to prevent fluid flow from the flow path into the pharmaceutical chambers;

a user actuated delivery valve operably coupling the flow path and the needle assembly, the delivery valve preventing fluid flow from the flow path into the needle assembly when in a closed position and the delivery valve permitting fluid flow from the flow path into the needle assembly when in an open position;

means for selecting a dose of each of the liquid pharmaceuticals to be delivered through the needle assembly; and means for automatically driving the pistons against the liquid pharmaceuticals within the pharmaceutical chambers, thereby reducing the volumes of the pharmaceutical chambers and driving the pistons distances corresponding to the selected doses, after the dose selecting step and upon switching the delivery valve from the closed position to the open position, whereby the dose of each liquid pharmaceutical is generally simultaneously delivered through the needle assembly.

29. The dispenser of claim 28 further comprising bypass means for allowing a liquid pharmaceutical to be selectively aspirated into each of the pharmaceutical chambers while bypassing the check valves.

30. The dispenser of claim 29 wherein the bypass means includes:

supplemented pathways fluidly coupling the flow path and the pharmaceutical chambers while bypassing the check valves; and aspiration valve means for selectively sealing the supplemental pathways.

31. The dispenser of claim 28 wherein:

the delivery valve includes a delivery check valve positioned along the flow path, the delivery check valve including a valve seat and a movable element biased against the valve seat; and the needle assembly includes a double ended needle cannula movably mounted to the body for movement between a predelivery position and a delivery position, the needle cannula being configured to engage the movable element and move the movable element away from the valve seat when the needle cannula is moved from the predelivery position to the delivery position thereby permitting free flow of fluid from the flow path to the needle cannula.

32. The dispenser of claim 28 further comprising:

a shield slidably mounted to the body movable between a safe position covering the needle assembly and a use position exposing at least a portion of the needle assembly; and means for temporarily securing the shield in the safe position.

33. The dispenser of claim 28 wherein the dose selecting means includes:

rotatable dose adjusters each having first threads;

stems each having second threads which matingly engage the first threads; and means for preventing the stems from rotating within the body so that rotation of the dose adjusters cause relative axial movement between the stems and the associated dose adjusters.

34. The dispenser of claim 28 further comprising:

a user viewable rotary display disc mounted to the base; and rack and pinion means for threadably coupling the display disc to the dose selection means so that axial movement of the dose selection means causes corresponding rotary motion of the display disc.

35. A multiple pharmaceutical cartridge-type assembly comprising:

hollow cylinders and an axially moveable piston within each cylinder, each piston and hollow cylinder defining a variable volume pharmaceutical chamber;

a flow path element coupling the hollow cylinders to one another and fluidly coupling the pharmaceutical chambers to an outlet;

a check valve associated with each of the pharmaceutical chambers and positioned along the flow path, the check valves configured to permit fluid flow from the pharmaceutical chambers into the flow path but to prevent fluid flow from the flow path into the pharmaceutical chambers; and a user actuated delivery valve operably coupling the flow path and the outlet, the delivery valve preventing fluid flow from the flow path into the outlet when in a closed position and the delivery valve permitting fluid flow from the flow path into the outlet when in an open position.

36. The assembly of claim 35 further comprising bypass means for allowing a liquid pharmaceutical to be selectively aspirated into each of the pharmaceutical chambers while bypassing the check valves.

37. The assembly of claim 36 wherein the bypass means includes:

supplemented pathways fluidly coupling the flow path and the pharmaceutical chambers while bypassing the check valves; and aspiration valve means for selectively sealing the supplemental pathways.

* * * * *